United States Patent [19]

Gray et al.

[11] Patent Number: 5,389,536
[45] Date of Patent: Feb. 14, 1995

[54] **LIPASE FROM *PSEUDOMONAS MENOCINA* HAVING CUTINASE ACTIVITY**

[75] Inventors: Gregory L. Gray, Boise, Id.; Scott D. Power, San Bruno; Ayrookaran J. Poulose, Belmont, both of Calif.

[73] Assignee: Genencor, Inc., Rochester, N.Y.

[21] Appl. No.: 705,052

[22] Filed: May 23, 1991

Related U.S. Application Data

[63] Continuation-in-part of Ser. No. 629,308, Dec. 18, 1990, abandoned, which is a continuation-in-part of Ser. No. 465,532, Jan. 17, 1990, abandoned, which is a continuation of Ser. No. 107,902, Oct. 19, 1987, abandoned, which is a continuation-in-part of Ser. No. 932,959, Nov. 19, 1986, abandoned.

[51] Int. Cl.⁶ ............................................. C12N 9/20
[52] U.S. Cl. .................................. 435/198; 435/195; 435/172.3; 935/14; 930/240
[58] Field of Search ............................. 435/198, 195

[56] References Cited

U.S. PATENT DOCUMENTS 4,665,029  5/1989  Iwai et al. ........................... 435/198

FOREIGN PATENT DOCUMENTS 0188072  9/1985  Japan ................................... 435/198

OTHER PUBLICATIONS

Suigiura, M., "Bacterial Lipases", In: *Lipases*, Borgström and Brockman (eds) Elsevier; Amsterdam, New York, Oxford; 1984.

Macrae, A. R., "Extracellular Microbial Lipases", In: *Microbial Enzymes and Biotechnology*, Fogarty, W. (ed); Applied Science Publishers, N.Y. 1984.

*Primary Examiner*—Marian Knode
*Attorney, Agent, or Firm*—Margaret A. Horn

[57] ABSTRACT

A substantially enzymatically pure hydrolase is provided which is secreted by and isolatable from *Pseudomonas mendocina* ATCC 53552. Cloning the gene expressing the hydrolase into a suitable expression vector and culturing, such as fermenting the *E. coli* strain JM101 harboring a plasmid designated pSNtacII, has been found to provide surprisingly high yields of the hydrolase.

1 Claim, 1 Drawing Sheet

LIPASE FROM *PSEUDOMONAS MENOCINA* HAVING CUTINASE ACTIVITY

CROSS REFERENCE TO RELATED APPLICATIONS

This application is a continuation-in-part of U.S. patent application Ser. No. 629,308, filed Dec. 18, 1990, (abandoned), which is a continuation-in-part of U.S. patent application Ser. No. 465,532, filed Jan. 17, 1990, (abandoned), which is a File Wrapper Continuation of U.S. patent application Ser. No. 107,902, filed Oct. 19, 1987, (abandoned), which is a continuation-in-part of U.S. patent application Ser. No. 932,959, filed Nov. 19, 1986 (abandoned).

FIELD OF THE INVENTION

The present invention generally relates to enzymes, and more particularly relates to a novel hydrolase, isolatable from *pseudomonas mendocina* ATCC 53552 and purifiable as a substantially enzymatically pure peptide, and a method for producing the hydrolase by cloning.

BACKGROUND OF THE INVENTION

Pseudomonas is a genus of short, rod-shaped bacteria. Several strains have been shown to have a limited ability to grow on a minimal media with mono-oleate polyoxyethylene ("Tween 80", available from Atlas Chemical) as carbon source. Howe et al., *J. Gen. Microbiol.*, 92(1), pp. 234–235 (1976). Various uses have been described for strains belonging to the genus Pseudomonas although none specifically referenced *P. mendocina*.

U.S. Pat. No. 4,385,112, issued May 24, 1983, inventors Misaki et al., discloses use of a microorganism strain belonging to the genus Pseudomonas isolated from a soil sample from an onion field in Japan to produce a nucleoside oxidase useful for enzymatic reactions involving various nucleosides.

In short, novel strains of *Pseudomonas mendocina* producing various enzymes have recently been discovered for a variety of applications.

SUMMARY OF THE INVENTION

In one aspect of the present invention, a novel enzyme is provided with hydrolase activity. This hydrolase is secreted by *Pseudomonas mendocina* ATCC 53552 and is isolatable as a substantially enzymatically pure peptide. In another aspect of the present invention, the novel hydrolase is produced in high yield by cloning the gene expressing the hydrolase into a suitable expression vector, and culturing to express the gene for the hydrolase. The enzyme has the following amino acid sequence:

```
01                10                20
A P L P D T P G A P F P A V A N F D R S G P Y T T S S Q 30           41             50
S E G P S C R I Y R P R D L G Q G G V R H P V I L W G 60              70              81
N G T G A G P S T Y A G L L S H W A S H G F V V A A A 90               100
E T S N A G T G R E M L A C L D Y L V R E N D T P Y G 110            121              130
T Y S G K L N T G R V G T S G H S Q G G G G S I M A G
```

-continued
```
140              150              161
Q D T R V R T T A P I Q P Y T L G L G H D S A S Q R R Q 170              180              190
Q G P M F L M S G G G D T I A F P Y L N A Q P V Y R R 201              210
A N V P V F W G E R R Y V S H F E P V G S G G A Y R G 220              230              241
P S T A W F R F Q L M D D Q D A R A T F Y G A Q C S L 250              260              270
C T S L L W S V E R R G L
```

The novel hydrolase is useful in a variety of applications, such as in biomass processing for breakdown of cellular materials (e.g. cutin and the like) and in enzymatic perhydrolysis for laundry and bleaching.

DESCRIPTION OF THE PREFERRED EMBODIMENTS

Figure 1:
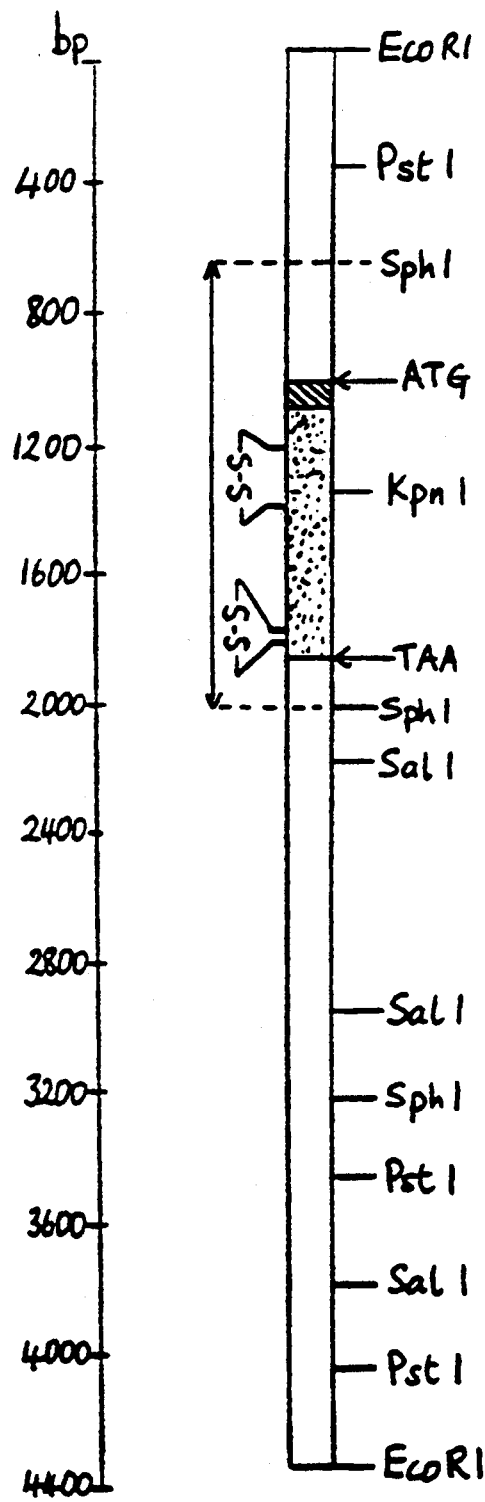
FIG. 1 is a map of the 4.3 kb EcoRI fragment of a plasmid designated pSNE4. The region crosshatched represents signal peptide codons (codons −22 to +1) and the stippled region indicates the coding region (codons +1 to +258) for the mature polypeptide designated Lipase 1. The ATG initiation codon and TAA stop codon are also marked.

In order to ensure proper understanding and interpretation of the invention, including the summary and preferred embodiments as well as the claims, some definitions are set forth below to clarify the use of terms employed herein. The defined terms include the following:

"Perhydrolysis" is defined as the reaction of a selected substrate with peroxide to form a peracid and water.

"Enzymatic perhydrolysis" is defined as a perhydrolysis reaction which is assisted or catalyzed by an enzyme generally classified as a hydrolase, and more specifically identified below.

The novel enzyme (sometimes herein referred to as "Lipase 1") is secreted by and isolatable from *Pseudomonas mendocina*. A culture of a novel *Pseudomonas mendocina* strain from which the Lipase 1 enzyme may be isolated has been deposited in accordance with MPEP 608.1(P) in the permanent culture collection of the American Type Culture Collection, 12301 Parklawn Drive, Rockville, Md. 20852, and has been designated ATCC 53552.

It should be understood that the microorganism of the present invention is not limited to the *Pseudomonas mendocina* strain hereinabove described, as natural and artificial mutants of the said microorganism can be used. Mutant or variant strains of *Pseudomonas mendocina* ATCC 53522 may be obtained by environmental selection pressure techniques, by UV irradiation, or by the use of mutagenic chemicals. As described hereinafter, genetic engineering techniques applicable to hydrolase production, such as transformation of corresponding genes of the present strain to other cells, are preferably applied for commercial production of the hydrolase.

However, the *Pseudomonas mendocina* strain may be cultured in a conventional medium. Liquid or solid culture can be used. Submerged aeration culture is preferable. A conventional nutrient medium can be used. Culturing temperature may vary depending on the desired rate of growth of the microorganisms and is preferably at 25°–35° C. Culturing time can be selected as desired, and is 15–50 hours. Culturing may be terminated when the highest concentration of hydrolase is present in the medium.

Hydrolase is accumulated in the fermentation broth, and extraction of the produced enzyme from the broth can be effected as follows. Cells and cell debris are first removed from the whole cell broth culture by microfiltration and centrifugation, followed by ultrafiltration to concentrate the hydrolase. Excess salts and color are then removed by dialysis or diafiltration.

The crude enzyme solution can then be purified. A powder of the enzyme can be obtained by lyophilization and used in the various applications.

The Lipase 1 has the following amino acid sequence:

```
01           10              20
A P L P D T P G A P F P A V A N F D R S G P Y T T S S Q 30           41            50
S E G P S C R I Y R P R D L G Q G G V R H P V I L W G 60            70             81
N G T G A G P S T Y A G L L S H W A S H G F V V A A A 90              100
E T S N A G T G R E M L A C L D Y L V R E N D T P Y G 110           121             130
T Y S G K L N T G R V G T S G H S Q G G G G S I M A G 140           150            161
Q D T R V R T T A P I Q P Y T L G L G H D S A S Q R R Q 170           180           190
Q G P M F L M S G G G D T I A F P Y L N A Q P V Y R R 201           210
A N V P V F W G E R R Y V S H F E P V G S G G A Y R G 220           230             241
P S T A W F R F Q L M D D Q D A R A T F Y G A Q C S L 250           260            270
C T S L L W S V E R R G L
```

Preferably, the hydrolase is produced by genetic manipulation techniques, for example by the transfer of plasmid DNA to a multicopy host or by the excision of the chromosomal genes coding for the hydrolase from the cells of a hydrolase producing bacteria, followed by the cloning of said genes into a suitable vector molecule. A preferred means of producing Lipase 1 is by cloning.

Thus, and as further described in Example 9, FIG. 1 is a map of the 4.3 kb ExoRI fragment of pSNE4. The crosshatched box represents the signal peptide codons (codons −22 to +1), and the stippled region indicates the coding region for the mature Lipase 1 polypeptide codons +1 to +258. The postulated disulfide bonds are shown. The scale is in base pairs (bp). The region sequenced (an SphI fragment of 1363 bp) is indicated with a double arrow. The ATG initiation codon and TAA stop codon are also marked.

Lipase 1 has excellent hydrolytic activity and can be used to produce peracid from a suitable substrate (for example, a triglyceride such as trioctanoin) in the presence of a peroxide source. It can produce peracid even in the presence of anionic surfactants, which typically inhibit the activity of enzymes. The use of this novel enzyme to produce peracid, for applications such as bleaching, is described and claimed in co-pending U.S. application Ser. No. 932,717, filed Nov. 19, 1986, entitled "ENZYMATIC PERACID BLEACHING SYSTEM".

When produced by fermentation of the *P. mendocina* strain, the Lipase 1 preferably is separated from other proteins and purified by means known to the art, such as by ion exchange and gel permeation chromatography, to yield substantially enzymatically pure Lipase 1. This is primarily because the crude fermentation broth of *P. mendocina* was found to include another enzyme (hereinafter "Lipase 2") in addition to Lipase 1.

Lipase 1 and Lipase 2 may be separated by means known to the art such as chromatography. They can be distinguished by their different hydrolysis rates for p-nitrophenyl butyrate and p-nitrophenyl caprylate.

Lipase 1 preferably is produced by cloning to express this enzyme through a host organism, such as a bacteria, yeast, or fungi by techniques known to those skilled in the art. Especially preferred is cloning in *E. coli*, followed by column chromatography of the cloned Lipase 1, as is more particularly described hereinafter. Production by cloning in accordance with the invention provides surprisingly high yields. Thus, the yield recoverable from fermentation broth of *E. coli* strain JM101 harboring the plasmid pSNtacII, as described in Example 9, has been found to be up to about 5.5 g/liter, with about 3.4 g/liter being an average yield. These yields are surprisingly high, since conventional amounts of peptide recovery from *E. coli* fermentation are on the order of about 0.2–0.3 g/liter. That is, practice of the inventive method can provide about ten times greater yield of the novel hydrolase than could have generally been expected.

Lipase 2 is also novel, hydrolzyes glyceride substrates, and may be used in applications such as in fats and oils processing as a digestive aid.

The following experimental methods, materials and results are described for purposes of illustrating the present invention. However, other aspects, advantages and modifications within the scope of the invention will be apparent to those skilled in the art to which the invention pertains.

EXPERIMENTAL

EXAMPLE 1

(A) Seeding and Fermenting

A seed medium was prepared with 0.6% nutrient broth (Difco) and 1% glucose (pH 6.5). 100 ml of this medium was sterilized in 500 ml fernbach flasks. The flasks were each seeded with a loopful from an overnight culture of *P. mendocina* ATCC 53552 grown on nutrient agar, and placed on a Newbrunswick shaker at 250 rpm, 37° C. for 12 hours. The incubated 12-hour culture was then seeded at appropriate volumes (1–10% v/v) into a 1 liter fermenter (250 ml working volume), a 15 liter Biolafitte fermenter (12 liters working volume), or a 100 liter Biolafitte fermenter provided with a temperature controller, RPM, airflow and pressure controller. The fermenter medium contained 0.6% nutrient broth (Difco), 0.3% apple cutin, and 0.2% yeast extract (Difco), with an initial pH of 6.5. The medium was adjusted to pH 6.8 and sterilized for 40 minutes before seeding. Bacterial growth and enzyme production were allowed to continue in the fermenter for 12–15 hours.

(B) Enzyme Recovery by Microfiltration

The crude fermentation culture was first filtered in an Amicon unit outfitted with two Romicon microporous membranes (0.22 u) to remove cells. Remaining enzyme in the retentate which was bound to the cutin particles was removed by centrifugation. Total recovery approached 90%.

(C) Concentration and Dialysis of Whole Cell Filtrate

The recovered filtrate from the Amicon unit was concentrated to a volume of 3 liters on an Amicon ultrafiltration unit with two Romicon F? 10 modules. The concentrated material was then dialised with 20 liters of 0.01M phosphate buffer, pH 7.5, to remove salts and color. Recovery at this stage averaged about 80%. Total activity for this crude preparation was $8.68 \times 10^6$ units. A unit of hydrolase activity is defined as the amount of enzyme which results in an increase of absorbance at 415 nm of 1.0/minute when incubated at 25° C. with 2.0 mM p-nitrophenylbutyrate in 0.1M pH 8.0 Tris-HCl buffer containing 0.1 wt. % Triton X-100.

EXAMPLE 2

Hydrolase Activity After

Ultrafiltration and Diafiltration

The binding of three p-nitrophenyl substrates and the turnover kinetics were studied for the crude preparation of Example 1 (C), where reaction conditions were 0.1M Tris with 0.1 wt. % Triton X-100, pH 8.0, at 25° C. The substrates were p-nitrophenyl caprylate, p-nitrophenyl laurate, and p-nitrophenyl palmitate, and the data is set out in Table 1.

TABLE 1

| Substrate | $K_m$ (μM) | $V_{max}$ (μmole/min/mg protein) |
|---|---|---|
| PNPC | 214 | 802 |
| PNPL | 167 | 214 |
| PNPP | 183 | 112 |

The Example 1(C) preparation was used in a variety of experiments; however, the Example 1(C) preparation includes two enzymes designated "Lipase 1" and "Lipase 2". Lipase 1 is the better perhydrolase. A separation and purification of the crude Example 1(C) preparation is described in Example 3, a complete separation of Lipase 1 and Lipase 2 is described in Example 4 (preferred to obtain substantially enzymatically pure Lipase 1), and an extremely pure sample of Lipase 1 preparation (i.e. analytically pure for sequencing) is described in Example 5.

EXAMPLE 3

Partial Purification of Lipase 1 and Lipase 2 by Ion Exchange and Gel Permeation Chromatography Lipase 1 was initially partially purified from *Pseudomonas mendocina* fermentation broth by DEAE Sephacryl chromatography followed by Sephadex G-100 gel permeation chromatography. A DEAE column was equilibrated in 10 mM sodium phosphate buffer, pH 8, and the crude protein was applied to the column in the same buffer. PNB (p-nitrophenyl butyrate) hydrolase activity that was not bound to the column was associated with Lipase 1. Lipase 1 thus obtained from the DEAE step was subjected to chromatography on Sephadex G-100 in 10 mM sodium phosphate buffer pH8. Lipase 1 eluted from this column as a discrete peak, and was identified by PNB hydrolase activity as well as perhydrolytic activity.

EXAMPLE 4

Complete Separation of Lipase 1 and Lipase 2 by Hydrophobic Chromatography

Lipase 1 may be separated completely from Lipase 2 by chromatography on hydrophobic resins. The enzyme solution of Example 1 (C) after ultrafiltration and diafiltration was adjusted to 0.5M NaCl and applied to a 0.8×7 cm octyl Sepharose column equilibrated in 10mM Tris (Cl) pH 8, 0.5M NaCl and washed to remove unbound protein. The following washes were then employed: 10 mM Tris (Cl), pH 8, 2M urea; 10 mM Na phosphate pH 8; 10 mM phosphate, pH 8, 0.5M NaCl. After washing, the column was then developed with a linear gradient to 50% n-propanol. The column fractions were then assayed for activity on p-nitrophenyl butyrate (PNB) and p-nitrophenyl caprylate (PNC) in order to locate the enzymatic activities. Two enzymes were clearly resolved, fraction 32 with a PNB/PNC ratio of 4.6 and fraction 51 with a PNB/PNC ratio of 1.40. These have been designated Lipase 1 and Lipase 2, respectively.

The fractions from this column were further analyzed by SDS gel electrophoresis. This analysis revealed that the two enzyme activities track with 30,000 molecular weight bands characteristic of procaryotic enzymes; in addition, Lipase 2 migrated as a doublet, and was clearly resolved from the single band of Lipase 1. Prior to sequence analysis, these two partially purified enzymes were separated from the high and low molecular weight contaminants by reverse phase chromatography.

EXAMPLE 5

Purification of Lipase 1 by HPLC in Preparation for Enzyme Peptide Fragmentation Prior to sequence analysis, the partially purified material of Example 3 was further purified by chromatography on a 4.8×100 mm, SynChromPak C4 reverse phase HPLC column. The system was equilibrated in 0.05% triethylamine (TEA) and 0.05% trifluoroacetic acid (TFA) (Solvent A) at 0.5 mL/min. 100 μg to 1 mg of Lipase 1 was injected onto the column and the protein eluted by a compound gradient of Solvent A and n-propanol containing 0.05% and 0.05% TFA (Solvent B). A typical gradient was +5% from 0 to 20% B and then +0.5% B/minute to 60% B. All enzyme is inactivated by this HPLC solvent system. The protein peaks eluting at about 35% solvent B (Lipase 1) or at about 39% Solvent B (Lipase 2) were collected and used for further sequence analysis and preparation of CNBr fragments.

EXAMPLE 6

Preparation and Purification of Cyanogen Bromide Peptide Fragments for Amino Acid Analysis The cyanogen bromide peptide fragments for amino acid sequence analysis were prepared and purified as follows. An aliquot of pooled Lipase 1 of Example 5 was dried in a SpeedVac centrifuge and then resuspended to 10 mg/ml in 8M urea, 88% formic acid. The solution was mixed with one volume of 200 mg/ml CNBr in formic acid and incubated in the dark at room temperature for 2 hours. The product was then desalted into 40% solvent B:50% solvent A (see above) on a 0.8×7 cm IBF-TrisAcryl GFO5 (coarse) column prior to reverse phase analysis. The peptides were initially separated using the same protocol as listed above for the purification of Lipase 1 by reverse phase. Solvent B, however, was changed to 35% propanol: 65% acetonitrile (containing TEA and TFA). The initial digest and the peaks after chromatography were also analyzed on SDS/urea/pyridine gels followed by silver staining.

Two peaks were chosen from the chromatogram and subjected to rechromatography employing the conditions dictated above, this time on a 0.48×25 cm SynChromPak C4 column. After rechromatography, the purified peptides were held for sequence analysis.

EXAMPLE 7

Distinction of Lipase 1 from Lipase 2: Preparation of Cyanogen Bromide Fragments of Lipase 1 and Lipase 2

The purified fractions of Lipase 1 and Lipase 2 from the octyl Sepharose column (as in Example 4) were each diluted with 3 volumes of solvent A (0.05% triethylamine and 0.05% triflouroacetic acid) and chromatographed (as in Example 5). As described in Example 4, the purified proteins were analyzed by SDS gel electrophoresis, and then pooled individually for comparison of the CNBr fragments and the N-terminal amino acid sequences of Lipase 1 & Lipase 2.

EXAMPLE 8

Specific Activity of Lipase 1

The specific activity of Lipase 1 was determined using the enzyme purified as in Example 4. Substantially enzymatically pure Lipase 1 has a specific enzyme activity of 3750 units per mg protein as defined in Example 1(C).

EXAMPLE 9

Preparation of Cloned Lipase 1 in *E. coli* Cloning of the Lipase 1 Gene of *Pseudomonas mendocina*

The *Pseudomonas mendocina* strain (ATCC 53552) was grown overnight at 37° C. in 200 ml LB (Luria Broth) medium. Cells were harvested by centrifugation and high molecular weight total DNA was prepared exactly according to a standard procedure as outlined by Birnboim et al., *Nucleic Acids Res.* 7, pp. 1513–1523 (1979). The DNA was digested to completion with EcoRI and ligated with T4 DNA ligase to a preparation of plasmid pER322 (ATCC 37107) digested with EcoRI and dephosphorylated with bacterial alkaline phosphatase. All enzymes used for the manipulation of DNA were used according to the manufacturers' directions (New England Biolabs or Bethesda Research Laboratories). The ligated DNA was used to transform *E. coli* 294 (ATCC 31445) and ampicillin resistant (Ampr) colonies were selected. Accordingly, approximately $2 \times 10^4$ transformants were obtained (approximately $5 \times 10^3$/plate). Plates were flooded with a solution of 4-methylumbelliferylbutyrate (10 mM in 50 mM Tris-HCl, pH 8.0) and then illuminated with an ultraviolet lamp (wavelength 340 nm). Colonies which hydrolyzed the substrate to release the highly flourogenic compound 4-methylumbelliferone appeared as intensely blue. Using this method 13 positive colonies were obtained. From each of these positive colonies a plasmid miniprep was prepared by the alkaline lysis method as described in Birnboim, supra. Each plasmid was digested with EcoRI and resulting fragments were resolved by polyacrylamide gel electrophoresis as described by Maniatis et al., *Molecular Cloning: A Laboratory Manual*, Cold Spring Harbor Laboratory, Cold Spring, N.Y. (1982). Most plasmids contained a single inserted fragment of 4.3 kb. The others contained other fragments in addition to this fragment. This result suggested that all positive colonies arose as a result of the expression of a common cloned gene contained on the 4.3 kb fragment. One of the plasmids which contained only the 4.3 kb fragment, designated pSNE4, was selected for detailed analysis.

Plasmid pSNE4 was digested with a variety of restriction enzymes which have 6 bp recognition sequences. These enzymes were used singly or in pairs. Analysis of the fragment sizes resulting from these experiments allowed the generation of a preliminary restriction endonuclease cleavage map of the 4.3 kb EcoRI insert of PSNE4. This map is shown in FIG. 1.

Several subfragments of the EcoRI insert of plasmid PSNE4 which were at least 840 bp were subcloned into pBR322 in order to see if any contained a functional gene. Among the plasmids which were found to contain functional hydrolase genes was pSNES1, which contains a 2.3 kb EcoRI/SalI fragment from the EcoRI insert of pSNE4. (See FIG. 1 for map location of this fragment).

The inserted fragment of pSNES1 was digested with further restriction enzymes and the resulting small fragments were subcloned into bacteriophage M13 vectors, described by Roberts, *Nucleic Acids Res.*, 12, supplement r167–r204 (1984), for sequencing by the dideoxy chain termination method of Sanger et al., *Proc Natl. Acad. Sci. USA* 74, pp. 5463–5467 (1977). The sequence of the 1.36 kb of DNA between the SphI sites (refer to FIG. 1), when translated in all possible reading frames, revealed a large open reading frame which includes the NF2-terminal amino acid residues of the protein as determined by direct amino acid sequencing (residues 1–16). This open reading frame also contains the code for two other directly sequenced peptides (residues 94–105 and residues 173–190). The methionine at position −22 is believed to be the initiation codon because it begins the code for a highly hydrophobic region typical of signal peptides. This signal peptide is presumably cleaved off during the secretion process after the alanine at position −1. The open reading frame ends at position 259, indicating that the encoded mature protein has 258 residues.

Regulated Expression of *P. mendocina* Lipase 1 Gene in *E. coli*

In order to achieve the regulated expression of the *P. mendocina* hydrolase gene in *E. coli*, an XbaI site was first introduced just before the ATG initiation codon by site directed mutagenesis, Adelman et al., DNA 2, PP.

183-193 (1983) in bacteriophage M13, and the modified gene was subsequently cloned into an expression vector which contains the strong tacII promoter, deBoer et al., Proc. Natl. Acad. Sci. USA 80, p. 2125 (1983). This was done by first digesting pSNES1 with SphI.

The 2.4 kb SphI fragment containing the entire hydrolase coding sequence was isolated and ligated into the replicative form (RF) of M13mp19 at its ,SphI site and the mixture was used to transfect E. coli JM101 (ATCC 33876). Clear plaques were picked and the bacteriophage (template) DNA in which the SphI fragment was present in a counterclockwise orientation was prepared. A partially complementary single-stranded fragment of DNA consisting of 50 nucleotides was synthesized which contained an XbaI site immediately 5' of the Lipase 1 ATG initiation codon. This 50-mer complements the template DNA from the −27 nucleotide position (before the ATG initiation codon) to the −9 position and from the +1 (the A of the ATG) to the +20 position. Between the −9 and the +1 positions, however, the sequence 5'-AACCITOG-3' of the native hydrolase promoter region was to be changed to 5'-TATCTAGAATT-3' of the tacII promoter. Mutagenesis was performed.

Figure 2:
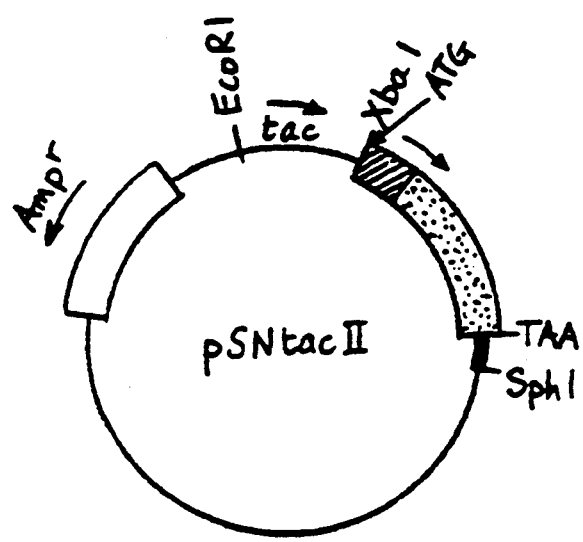
FIG. 2 illustrates an *E. coli* expression vector for Pseudomonas Lipase 1 gene. The stippled region indicates the coding region for the hydrolase signal sequence of 22 amino acids. The crosshatched region indicates the coding region for the mature hydrolase protein. Transcription starts at the ATG initiation codon and proceeds in the direction indicated by the arrow to the TAA stop codon. The dark regions on either side indicate the 5'- and 3'-untranslated regions.

Three hundred plaques were screened by hybridization with a $^{32}$p-labeled synthetic oligonucleotide (5'-ATGAGGTATCTAGAATTATG-3') which spans the area of change. An RF of a positively hybridizing clone was prepared and cleaved with XbaI and SphI. A 1 kb XbaI/SphI fragment containing the gene was isolated and ligated into a vector obtained by digesting pHGH907tacII, described by deBoer, supra, with XbaI and SphI and isolating a 4.1 kb XbaI/SphI fragment containing the tacII promoter, and the ampicillin resistance gene. JM101 cells were then transformed with the ligation mixture. An ampicillin resistant colony (containing plasmid pSNtacII—see FIG. 2) was selected.

To determine the levels of cloned Lipase 1 synthesized by E. coli, JM101/pSNtacII was grown in 20 mls LB medium supplement with 1 mM isopropyl-B-D-thiogalactoside (IPTG) for 10 h at 37° C. 294/pBR322 was used as a negative control. The cells were separated from the culture supernatant by centrifugation and then fractionated into periplasmic and membrane/cytoplasmic components, Koshland, supra. Each fraction was tested for activity by p-nitrophenylbutyrate hydrolysis. β-lactamase (periplasmic marker) and β-galactosase (cytoplasmic marker) were also measured, Gray et al., Proc. Natl. Acad. Sci. USA .81, pp. 2645–2649 (1984), in order to confirm the effectiveness of the cell fractionation procedure.

Most of the Lipase 1 activity (74%) was present in the culture supernatant. Most of the cell associated enzyme was found in the cell was fraction (17% of the total) with smaller amounts present in the periplasmic (2%) and cytoplasm/membrane (7%) fractions. No Lipase 1 activity was present in any fractions of the 294/pBR322 negative control culture. Yields of Lipase 1 in eight fermentations as just described (10 liter fermenters) were between 1.5 g/liter and 5.5 g/liter, for an average yield of 3.4 g/liter.

Broth from the fermentation of E. coli strain JM101 harboring the plasmid pSNtacII was adjusted to 0.5M NaCl and purified by octyl Sepharose substantially as described when P. mendocina is fermented (Example 4), except the propanol gradient was eliminated and elution was achieved with 20% acetonitrile in 10 mM Na phosphate, pH 8, 0.5M NaCl. The isolated product (cloned from the gene expressing the enzyme) was analyzed by SDS gels and migrated identically to the Lipase 1 product isolated from the original Pseudomonas mendocina strain.

EXAMPLE 10 Preparation of Cyanocen

Bromide Fragments from Cloned Lipase 1

Cyanogen bromide fragments from cloned Lipase 1 were prepared as follows. The product from the octyl Sepharose purification of cloned product (Example 9) was diluted with 3 volumes of solvent A and purified on the short C4 HPLC column, as described for Lipase 1 and Lipase 2 isolated from Pseudomonas mendocina. The product was analyzed on SDS gel.

EXAMPLE 11

Comparison of CNBr Fragments of Lipase 1 from P. mendoncina and CNBr Fragments from the Cloned Lipase 1 in E. coli CNBr fragments of Lipase 1 from P. mendocina and CNBr fragments from the cloned Lipase 1 in E. coli were compared. HPLC purified Lipase 1 and 2 from Pseudomonas and the cloned Lipase 1 were each hydrolyzed by CNBr as described in Example 6 above. The products were analyzed by SDS/urea/pyridine electrophoresis. The results indicate the cloned protein is clearly Lipase 1. Lipase 1 isolated from P. mendocina (as in Examples 4–5) was shown to be identical to the cloned Lipase 1 isolated from E. coli by the following criteria: (a) Lipase 1 from either organism was isolated by the same chromatographic procedure (as in Example 4); (b) the amino acid sequences of the N-terminal of the Lipase 1 isolated from either organism were the same; (c) the CNBr fragment pattern showed that the Lipase 1 and Lipase 2 are clearly distinguished and that the CNBr fragments of Lipase 1 from either P. mendocina or E. coli are identical; (d) the p-nitrophenyl butyrate and p-nitrophenylcaprylate substrate activity ratio of Lipase 1 from both bacterial sources is the same; and (e) the hydrolysis/perhydrolysis ratio with tricaprylin as substrate is the same for Lipase 1 as isolated from both organisms.

When separated, Lipase 1 and Lipase 2 were found to have quite different hydrolysis rates (hydrolytic activity) for p-nitrophenyl butyrate and for p-nitrophenyl caprylate. Thus, the two novel enzymes can be distinguished by their ratios of p-nitrophenyl butyrate to p-nitrophenyl caprylate hydrolysis, as illustrated by Example 12.

EXAMPLE 12

Lipase 2 with p-Nitrophenyl Butyrate and p-Nitrophenyl Caprylate as Substrates

The reactions were performed in samples containing 0.1M Tris HCl, pH 8.0 with 0.1 wt. % Triton X-100 nonionic surfactant (available from Rohm & Haas) at 25° C. The hydrolysis rates of 2.0 mM p-nitrophenyl butyrate (PNB) for Lipase 1 (as from Example 3), was 0.60 (OD 415 nm/min. ), while that of 2.0 mM p-nitrophenyl caprylate (PNC) was 0.09, for a PNB/PNC ratio of 7. By contrast, the hydrolysis rate of PNB for Lipase 2 at the same concentration was 0.54, of PNC at the same concentration was 0.44, for a PNB/PNC ratio of 1.

Example 13 illustrates stain removal studies using Lipase 1.

EXAMPLE 13

Diagnostic evaluations of oxidant performance were performed with 100% cotton swatches stained with crystal violet as follows. Crystal violet (0.125 g) was added to 1.25 liters of distilled water. One hundred two-inch by two-inch undyed, 100% cotton swatches were added to the solution and agitated for eight hours. The cotton swatches (now dyed with crystal violet) were removed from the staining solution and rinsed repeatedly with cold tap water until the effluent was nearly clear. The stained swatches were then individually placed on aluminum foil, blotted with paper towels, and allowed to air dry.

A formulation utilizing Lipase 1 was prepared, as was a corresponding control composition. Both compositions were each used to wash the stained cotton swatches and the stain removal performance evaluated for each. The performance results are summarized in Table 2.

TABLE 2

|  | Relative Stain Removal |
|---|---|
| Composition with Lipase 1 |  |
| 0.06 wt. % trioctanoin | 80.4 |
| 0.04 wt. % sodium dodecylsulfate |  |
| 200 ppm $H_2O_2$ |  |
| 1 µg/ml Lipase 1 |  |
| 20 µM EDTA |  |
| (pH = 10.5) |  |
| Control Composition |  |
| 0.06 wt. % Trioctanoin | 69.8 |
| 0.04 wt. % sodium dodecylsulfate |  |
| 200 ppm $H_2O_2$ |  |
| 20 µM EDTA |  |
| (pH = 10.5) |  |

As may be seen from the data of Table 2, the composition including Lipase 1 provided improved stain removal benefits with respect to the control composition even though the control composition included the hydrogen peroxide component. This improved stain removal was particularly striking as occurring in the presence of anionic surfactant which inhibits many prior known commercially available enzymes.

While the invention has been described in connection with specific embodiments thereof, it will be understood that it is capable of further modifications, and this application is intended to cover any variations, uses or adaptations of the invention following, in general the principles of the invention and including such departures from the disclosure as come within the known or customary practice in the art to which the invention pertains and as may be applied to the essential features hereinbefore set forth, and as fall within the scope of the invention and the limits of the appended claims.

We claim:

1. A lipase isolated from *Pseudomonas mendocina* having the following characteristics
   (a) cutinase activity; and
   (b) the amino acid sequence:

```
01            10            20
A P L P D T P G A P F P A V A N F D R S G P Y T T S S Q 30            41            50
S E G P S C R I Y R P R D L G Q G G V R H P V I L W G 60            70            81
N G T G A G P S T Y A G L L S H W A S H G F V V A A A 90            100
E T S N A G T G R E M L A C L D Y L V R E N D T P Y G 110           121           130
T Y S G K L N T G R V G T S G H S Q G G G G S I M A G 140           150           161
Q D T R V R T T A P I Q P Y T L G L G H D S A S Q R R Q 170           180           190
Q G P M F L M S G G G D T I A F P Y L N A Q P V Y R R 201           210
A N V P V F W G E R R Y V S H F E P V G S G G A Y R G 220           230           241
P S T A W F R F Q L M D D Q D A R A T F Y G A Q C S L 250           260           270
C T S L L W S V E R R G L.
```

\* \* \* \* \*